United States Patent
Borish et al.

(10) Patent No.: US 11,813,344 B2
(45) Date of Patent: Nov. 14, 2023

(54) ALKYL BENZOATE SOLUBILIZED ORGANIC SUNSCREEN FILTERS

(71) Applicant: Ethox Chemicals, LLC, Greenville, SC (US)

(72) Inventors: Edward T. Borish, Greenville, SC (US); Charles V. Hinton, Greenville, SC (US); Charles F. Palmer, Jr., Greenville, SC (US); Stephanie Anderson, Greenville, SC (US); Robert W. Howell, Greenville, SC (US)

(73) Assignee: ETHOX CHEMICALS, LLC, Greenville, SC (US)

( * ) Notice: Subject to any disclaimer, the term of this patent is extended or adjusted under 35 U.S.C. 154(b) by 161 days.

(21) Appl. No.: 17/181,409

(22) Filed: Feb. 22, 2021

(65) Prior Publication Data

US 2021/0259938 A1    Aug. 26, 2021

Related U.S. Application Data

(60) Provisional application No. 62/980,484, filed on Feb. 24, 2020.

(51) Int. Cl.
*A61K 8/37* (2006.01)
*A61K 8/35* (2006.01)
*A61Q 17/04* (2006.01)
*A61K 8/40* (2006.01)

(52) U.S. Cl.
CPC .............. *A61K 8/37* (2013.01); *A61K 8/35* (2013.01); *A61K 8/375* (2013.01); *A61K 8/40* (2013.01); *A61Q 17/04* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 6,350,894 | B1 | 2/2002 | Bonda et al. |
| 8,153,106 | B1 * | 4/2012 | Lott ........ A61Q 17/04 424/59 |
| 8,329,147 | B2 | 12/2012 | Ansmann et al. |
| 2004/0028709 | A1 | 2/2004 | Kalyanavarathan et al. |
| 2005/0013781 | A1 | 1/2005 | Dueva-Koganov et al. |
| 2013/0243709 | A1 | 9/2013 | Hanson et al. |

OTHER PUBLICATIONS

ISA/US; International Search Report and Written Opinion prepared for PCT/US21/19016; dated Apr. 29, 2021.
https://www.badgerbalm.com; Broad Spectrum Sunscreen—UVA Protection; accessed Feb. 9, 2021.
Shell Chemicals LP; NEODOL(TM)25 Technical Datasheet; Primary Alcohol; Updated Jan. 2021.
PubChem; Compound Summary; Alcohols, C12-14, propoxylated; modified Nov. 12, 2022.
GuideChem; 1-Ridecanol (CAS No. 80206-82-2) Safety Data Sheet; Product name: Alcohols, C12-14; https://www.guidechem.com/msds/80206-82-2.html; retrieved Dec. 7, 2022.

* cited by examiner

*Primary Examiner* — Nannette Holloman
(74) *Attorney, Agent, or Firm* — Joseph T. Guy; Patent Filing Specialist Inc.

(57) ABSTRACT

An improved broad-spectrum sunscreen formulation is provided. The sunscreen formulation comprises at least one organic sunscreen filter, at least one of which avobenzone, and an alkyl benzoate comprising 25-55 mole % C12-14 alkyl benzoate and 45-75 mole % C12-C15 alkyl benzoate.

24 Claims, 1 Drawing Sheet

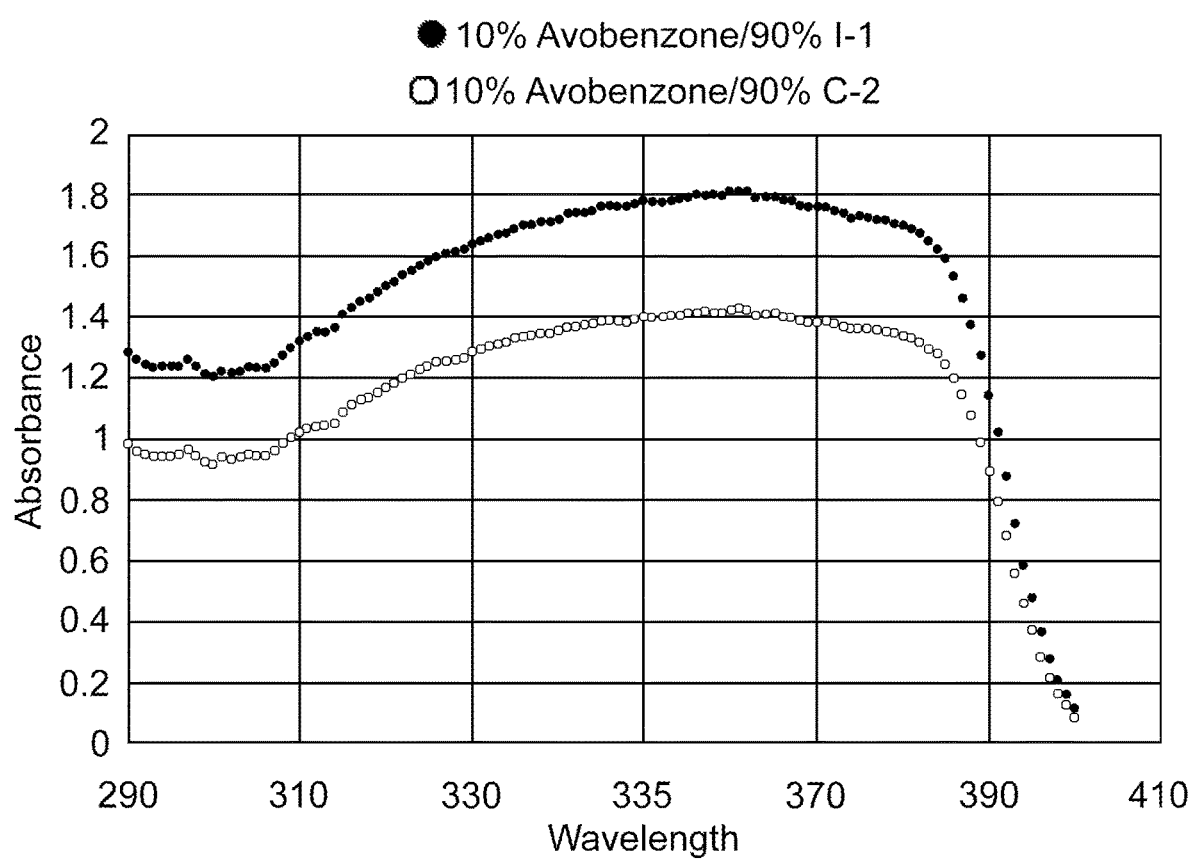

ALKYL BENZOATE SOLUBILIZED ORGANIC SUNSCREEN FILTERS

CROSS-REFERENCE TO RELATED APPLICATIONS

The present invention claims priority to U.S. Provisional Patent Application No. 62/980,484 filed Feb. 24, 2020 which is incorporated herein by reference.

FIELD OF THE INVENTION

The present invention is related to an improved sunscreen formulation, particularly, a sunscreen formulation comprising avobenzone as an organic sunscreen filter. More specifically, the present invention is related to a sunscreen formulation comprising avobenzone and a blended C12-14 and C12-15 alkyl benzoate which increases the sun protection factor (SPF) and provides broad-spectrum protection.

BACKGROUND

There is an on-going need for increased protection from the sun, particularly, for use by those that are in the sun for entertainment purposes or for those required to work in the sun for extended hours. Sunscreen formulations have been available for many decades wherein the sunscreen formulation is applied to the skin as a blocker of specific wavelengths of light.

Due to the extensive use of sunscreen formulations there has been a continual desire for sunscreen formulations which absorb more light per gram of sunscreen formulation and particularly those wavelengths of light considered to be most harmful to the skin. There has also been a desire to have sunscreen formulations which use organic sunscreen filters and which do not cause harm to ecosystems such as live reefs and other sensitive areas. Due to concerns about reef safety and toxicology surrounding oxybenzone and octinoxate, formulators are being asked to get more SPF protection from fewer organic sunscreen filters and higher concentrations of other organic sunscreen filters such as homosalate, octisalate, and octocrylene.

U.S. Pat. No. 8,329,147, which is incorporated herein by reference in its entirety, teaches the use of greater than or equal to 85 wt % C12 and C14 alkyl benzoates for cosmetic purposes. It has been surprisingly found that such high levels of C12 and C14 alkyl benzoates decreases the SPF of certain organic sunscreen filters such as avobenzone.

Provided herein is an improved sunscreen formulation wherein the SPF exceeds that of the prior art at the same use level of sunscreen filter.

SUMMARY OF THE INVENTION

The present invention is related to an improved sunscreen formulation.

More specifically, the present invention is related to improvements in the SPF of a sunscreen formulation, particularly comprising avobenzone, without detriment to the absorption of UV-A thereby providing a sunscreen formulation which meets the criteria of a broad-spectrum sunscreen.

A particular feature of the present invention is that the improved sunscreen formulation is more environmentally friendly while utilizing organic sunscreen filters.

These and other embodiments, as will be realized, are provided in a sunscreen formulation comprising at least one organic sunscreen filter, at least one of which is avobenzone, and alkyl benzoates comprising 25-55 mole % C12-14 alkyl benzoate and 45-75 mole % C12-C15 alkyl benzoate.

Yet another embodiment is provided in a sunscreen formulation comprising organic sunscreen filter comprising avobenzone and at least one additional organic sunscreen filter selected from the group consisting of octocrylene, homosalate and octisalate. The sunscreen formulation also comprises alkyl benzoates comprising 25-55 mole % C12-14 alkyl benzoate and 45-75 mole % C12-C15 alkyl benzoate. The sunscreen formulation has a critical wavelength of at least 370 nm.

BRIEF DESCRIPTION OF FIGURE

The FIGURE graphically illustrates an advantage of the invention.

DESCRIPTION

The present invention is related to an improved sunscreen formulation comprising avobenzone as an organic sunscreen filter, and optional additional organic sunscreen filters, solubilized in a blended C12-14 and C12-15 alkyl benzoate. C12-14 and C12-15 alkyl benzoate are also referred to in the art as C12-14 and C12-15 alkyl benzoate ester and the terms alkyl benzoate and alkyl benzoate ester are used interchangeably.

Throughout the present disclosure the term C12-14 alcohol refers to an alcohol comprising alkyl chains comprising 12-14 carbons, inclusively, and primarily 12 carbon alkyl chains and 14 carbon alkyl chains. C12-14 alcohol preferably has at least 65 mole % to no more than 75 mole % 12 carbon chains, at least 21 mole % to no more than 28 mole % 14 carbon chains and no more than 10 mole % 16 carbon chains with no appreciable amount, such as less than 2 mole %, of 13 carbon chains or 15 carbon chains. Similarly, the term C12-15 alcohol refers to an alcohol comprising alkyl chains comprising 12-15 carbons, inclusively, preferably including alkyl chains comprising 12, 13, 14 and 15 carbons. C12-15 alcohol comprises less than 1 mole % of 11 carbon and 16 carbon alkyl chains and at least 15 mole % to no more than 35 mole % of each of 12 carbon alkyl chains, 13 carbon alkyl chains, 14 carbon alkyl chains and 15 carbon alkyl chains, independently. The C12-14 alkyl benzoate and C12-15 alkyl benzoate are formed from the C12-14 alcohol and C12-15 alcohol, respectively, so the terms C12-14 alkyl benzoate and C12-15 alkyl benzoate have the same carbon chains as the alcohol from which they are formed A term such as C12 refers to 12 alkyl carbons. Therefore, the term C12 alcohol refers to an alcohol having 12 alkyl carbons. Similarly, the term C12 alkyl benzoate refers to an alkyl benzoate having 12 alkyl carbons.

It is particularly preferred that the blend of C12-14 alkyl benzoate and C12-15 alkyl benzoate comprise at least 25 mole % to no more than 55 mole % C12-14 alkyl benzoate and at least 45 mole % to no more than 75 mole % C12-15 alkyl benzoate. Alternatively, the final formulation has at least 22 mole % to no more than 67 mole % alkyl chains having 12 carbons.

An alkyl benzoate formed from blended C12-14 and C12-15 alcohol to solubilize avobenzone would not be expected to affect the SPF. Quite surprisingly, it was found that this alkyl benzoate formed from blended C12-14 and C12-15 alcohol actually doubles the SPF of avobenzone which was completely unexpected. An SPF boost with avobenzone is particularly advantageous since avobenzone imparts broad spectrum SPF to sunscreen formulations. Most formulators currently use C12-15 alkyl benzoate because it is a broad solubilizer for organic sunscreen filters, however there are new more effective ones in the marketplace that are better for the octocrylene, homosalate, and octrisalate organic sunscreen filters. Current commercial solublizers for organic sunscreen filters are effective with octocrylene, homosalate, and octisalate for SPF but have a negative impact on the SPF of avobenzone. The inventive alkyl benzoate allows for the use of less avobenzone in the formula to achieve a desired SPF. Alternatively, a higher SPF can be achieved with the same amount of applied sunscreen formulation. Alternatively, the inventive alkyl benzoate can be used with the new solubilizers that provide SPF in other organic sunscreen filters, but hinder avobenzone's broad spectrum SPF, thereby allowing formulators more versatility regarding which solubilizer they work with when formulating sunscreen formulations.

A 50/50 ratio of C12-14 alkyl benzoate to C12-15 alkyl benzoate doubles avobenzone SPF performance while maintaining the SPF level on other organic sunscreen filters. Additionally, it has been determined that the C12-14 alkyl benzoate to C12-15 alkyl benzoate ratio of 65:35 demonstrate a negative impact on all organic sunscreen filters.

The sunscreen formulation comprises 5-75 wt % organic sunscreen filter and 25-95 wt % alkyl benzoate with the organic sunscreen filter comprising at least avobenzone. More preferably the sunscreen formulation comprises 30-60 wt % organic sunscreen filter and 40-70 wt % alkyl benzoate with the organic sunscreen filter comprising at least avobenzone.

In-Vitro SPF Testing

The FDA 2011 method was used for testing the in-vitro SPF (LabSphere UV-2000S, North Sutton, N.H.) using 5 cm×5 cm polymethylmethacrylate (PMMA) plates (Helio-Screen HelioPlates HD6, Labsphere, North Sutton, N.H.). The PMMA plate was tared on an analytical balance with a readability of 0.001 grams. 2 mg/cm$^2$ of the mixture being tested (total of 0.05 g) was applied to the plate and, using a finger cot, the mixture was spread for a minute using circular, vertical, and horizontal motions to ensure complete coverage. Next, the plates were put into a dark drawer for fifteen minutes. Each plate was then scanned in five different locations. The software (UVS2000 Application, LabSphere, North Sutton, N.H.) measured absorbance and converted it to in-vitro SPF using an algorithm. The SPF of each of the five locations can be shown in the software, while the average SPF of the five locations can be exported. All absorbance values at each wavelength between 290-450 nm for all five locations can also be exported and analyzed. Lambda critical, standard deviations, and coefficients of variations are also included in the exported set. SPF is primarily a function of UV-B absorption of the formulation. Another critical component is UV-A protection which has proven difficult with organic sunscreen filters and therefore it has proven difficult to provide a sunscreen formulation designated as a broad-spectrum sunscreen utilizing organic sunscreen filters. Determination of the effectiveness of UV-A protection is defined by the critical wavelength which is the wavelength at which the sunscreen formulation allows 10% of the rays to penetrate. The United States Food and Drug Administration (FDA) recommends a critical wavelength over 370 nm as sufficient to provide excellent UVA protection.

Examples

A series of sunscreen formulations were prepared. An alkyl benzoate was prepared from a blend of C12-14 alcohol and C12-15 alcohol. Epal 1214 is a C12-14 alcohol which is commercially available as CAS 80206-82-2. Neodol 25 is a C12-15 alcohol which is commercially available as CAS 63393-82-8. In a first sample, referred to herein as I-1, the materials of Table 1 were combined and, using standard procedures known to one of ordinary skill in the art such as listed in U.S. Pat. No. 8,329,147, to form the alkyl benzoate having about 51 mole % C12-14 alkyl benzoate and about 49 mole % C12-15 alkyl benzoate.

TABLE 1

| Preparation of I-1 | |
| --- | --- |
| material | relative wt % |
| Epal 1214 | 33.7% |
| Neodol 25 | 28.3% |
| benzoic acid | 38.0% |

The molar ratio of chain lengths for I-1 is provided in Table 1A.

TABLE 1A

| chain length | totals |
| --- | --- |
| C12 | 48.50 |
| C13 | 13.05 |
| C14 | 24.45 |
| C15 | 11.25 |
| C16 | 2.75 |

A second sample, referred to herein as C-1, was prepared in similar fashion using the materials of Table 2 to form the alkyl benzoate having about 60 mole % C12-14 alkyl benzoate and about 40 mole % C12-15 alkyl benzoate.

TABLE 2

| material | relative wt % |
| --- | --- |
| Epal 1214 | 39.9% |
| Neodol 25 | 22.0% |
| benzoic acid | 38.1% |

The molar ratio of chain lengths for the formulation is provided in Table 2A.

TABLE 2A

| chain length | totals |
| --- | --- |
| C12 | 53.50 |
| C13 | 10.15 |
| C14 | 24.35 |
| C15 | 8.75 |
| C16 | 3.25 |

A series of sunscreen formulations were prepared with avobenzone, octocrylene, homosalate and octisalate as the organic sunscreen filter with I-1, C-1 or a commercially available C12-15 alkyl benzoate, such as Finsolve® TN from Innospec, used as a control and referred to as C-2. Each sample was tested for SPF with the results provided in Table 3 wherein all percentages are wt %.

TABLE 3

| Sample | Mean SPF | Std Dev. | Critical Wavelength (nm) |
|---|---|---|---|
| 90% I-1/10% Avobenzone | 21.61 | 3.61 | 382.8 |
| 90% C-1/10% Avobenzone | 9.43 | 1.06 | 382.8 |
| 90% C-2/10% Avobenzone | 10.95 | 2.18 | 382.6 |
| 50% I-1/50% Octocrylene | 20.71 | 4.57 | 357.6 |
| 50% C-1/50% Octocrylene | 10.90 | 1.75 | 356.2 |
| 50% C-2/50% Octocrylene | 24.18 | 5.87 | 357 |
| 50% I-1/50% Homosalate | 7.51 | 1.38 | 325.8 |
| 50% C-1/50% Homosalate | 7.98 | 1.28 | 326 |
| 50% C-2/50% Homosalate | 11.64 | 1.70 | 326.8 |
| 50% I-1/50% Octisalate | 10.71 | 0.80 | 326.8 |
| 50% C-1/50% Octisalate | 9.68 | 0.93 | 326.4 |
| 50% C-2/50% Octisalate | 8.56 | 1.19 | 326.4 |

The results presented in Table 3 demonstrate effective broad spectrum protection and a critical wavelength above the FDA recommended 370 nm. The invention illustrates a critical wavelength of at least 380 nm and even at least 382 nm.

In a separate experiment a combination with all 4 organic sunscreen filters was tested with each of I-1, C-1 and C-2. Each formulation comprised 30 wt % homosalate, 20 wt % octocrylene, 10 wt % octisalate, 6 wt % avobenzone and 34 wt % of one of I-1, C-1 or C-2. The in-vitro SPF was measured resulting in a mean SPF of 24.26 (Std. Dev. 3.10) for the combination of organic sunscreen filters in I-1, a mean SPF of 17.45 (Std. Dev. 4.26) for the combination of organic sunscreen filters with C-1 and a mean SPF of 24.64 (Std. Dev. 2.36) for the combination of organic sunscreen filters with C-2.

In a separate experiment, sunscreen formulations were made with each of I-1, C-1 and C-2 and the samples were tested for in-vitro SPF. The ingredients are listed in Table 4.

TABLE 4

| wt % | Ingredient | Phase |
|---|---|---|
| 44% | Water | A |
| 5% | Propanediol | B |
| 1% | Hydrolyzed Corn Starch Hydroxethyl Ether | B |
| 1% | Caprylhydroxamic Acid (and) Glyceryl Caprylate (and) Glycerin | B |
| 6% | Sodium Behenoyl Lactylate | C |
| 15% | Homosalate | D |
| 10% | Octocrylene | D |
| 5% | Octisalate | D |
| 3% | Avobenzone | D |
| 10% | I-1/C-1/C-2 | D |

The procedure for preparation included heating the mixture and maintain the temperature of A to 85° C. Premix B was then added to A with propeller stirring. Adding C to NB, stirring until uniform and smooth. Premix D was then heating until liquid and uniform. The mixture comprising A/B/C was removed from the heat and stirred until the temperature reaches around 60° C. Premix D was allowed to cool to close to room temperature after which D was added to A/B/C with propeller stirring until uniform and glossy. The mixture was gently stirred until the cream starts to set.

The in-vitro SPF results are reported in Table 5.

TABLE 5

| Sample | Mean SPF | Std Dev. |
|---|---|---|
| I-1 | 44.26 | 9.37 |
| C-1 | 38.03 | 6.68 |
| C-2 | 52.59 | 8.92 |

An alkyl benzoate formed from blended C12-14 and C12-15 alcohol to solubilize avobenzone would not be expected to affect the SPF. Quite surprisingly, it was found that this alkyl benzoate formed from blended C12-14 and C12-15 alcohol actually doubles the SPF of avobenzone which was completely unexpected. An SPF boost with avobenzone is particularly advantageous since avobenzone imparts broad spectrum SPF to sunscreens formulations. Most formulators currently use C12-15 alkyl benzoate because it is a broad solubilizer for organic sunscreen filters, however there are new more effective solubilizers available that are better for the octocrylene, homosalate, and octisalate organic sunscreen filters. Current commercial solublizers for organic sunscreen filters are effective with octocrylene, homosalate, and octisalate for SPF but have a negative impact on the SPF of avobenzone. The inventive alkyl benzoate allows for the use of less avobenzone in the sunscreen formulation to achieve a desired SPF or a higher SPF can be achieved with the same amount of applied sunscreen formulation. Alternatively, the inventive alkyl benzoate can be used with the new solubilizers that provide SPF in other organic sunscreen filters, but hinder avobenzone's broad spectrum SPF, thereby allowing formulators more versatility regarding which solubilizer they work with when formulating sunscreens. A 50/50 ratio of C12-14 alkyl benzoate to C12-15 alkyl benzoate doubles avobenzone SPF performance while maintaining the SPF level on other organic sunscreen filters. Additionally, it has been determined that the C12-14 alcohol to C12-15 alcohol ratio of 65:35 had a negative impact on all organic sunscreen filters.

Solvent/emollients not only show effectiveness at dissolving solid sunscreen actives, but also can shift and enhance the UV-absorbing capabilities of organic sunscreen actives. In all cases, and in combination, I-1 and C-2 showed similar results, and C-1 poorer numbers for SPF. Of particular relevance for struggling formulators is that I-1 appears to significantly enhance SPF when in combination with avobenzone compared to C-2, demonstrating an SPF of 22 instead of 11 without diminishing the Critical Wavelength which is 383 nm for both.

A comparison of the absorption of 10 wt % avobenzone in I-1 and 10 wt % avobenzone in C-2 is illustrated graphically in the FIGURE. Illustrated therein is the improvements in absorption in the UV-A region of 320-400 nm. The results illustrated graphically in the FIGURE, and numerically in Table 3, demonstrate the effectiveness of the inventive formulation as a broad-spectrum sunscreen.

The invention has been described with reference to the preferred embodiments without limit thereto. Additional embodiments and improvements may be realized which are not specifically set forth herein but which are within the scope of the invention as more specifically set forth in the claims appended hereto.

Claimed is:

1. A sunscreen formulation comprising:
   at least one organic sunscreen filter wherein said at least one organic sunscreen filter comprises avobenzone; and
   an alkyl benzoate comprising 25-55 mole % C12-14 alkyl benzoate and 45-75 mole % C12-C15 alkyl benzoate.

2. The sunscreen formulation of claim 1 comprising 5-75 wt % said at least one organic sunscreen filter and 25-95 wt % said alkyl benzoate.

3. The sunscreen formulation of claim 2 comprising 30-60 wt % said at least one organic sunscreen filter and 40-70 wt % said alkyl benzoate.

4. The sunscreen formulation of claim 1 comprising at least 22 mole % to no more than 67 mole % C12 alkyl benzoate.

5. The sunscreen formulation of claim 1 wherein said at least one organic sunscreen filter further comprises at least one additional organic sunscreen filter selected from the group consisting of octocrylene, homosalate and octisalate.

6. The sunscreen formulation of claim 5 wherein said at least one additional organic sunscreen filter comprises octocrylene.

7. The sunscreen formulation of claim 5 wherein said at least one additional organic sunscreen filter comprises homosalate.

8. The sunscreen formulation of claim 5 wherein said at least one additional organic sunscreen filter comprises octisalate.

9. The sunscreen formulation of claim 1 wherein said C12-C14 alkyl benzoate comprises at least 65 to no more than 75 mole % C12 alkyl benzoate and at least 21 to no more than 28 mole % C14 alkyl benzoate and no more than 10 mole % C16 alkyl benzoate.

10. The sunscreen formulation of claim 1 wherein said C12-C15 alkyl benzoate comprises at least 15 to no more than 35 mole % C12 alkyl benzoate; at least 15 to no more than 35 mole % C13 alkyl benzoate; at least 15 to no more than 35 mole % C14 alkyl benzoate and at least 15 to no more than 35 mole % C15 alkyl benzoate.

11. The sunscreen formulation of claim 1 having a critical wavelength of at least 370 nm.

12. The sunscreen formulation of claim 11 wherein said critical wavelength is at least 380 nm.

13. The sunscreen formulation of claim 12 wherein said critical wavelength is at least 382 nm.

14. A sunscreen formulation comprising:
    organic sunscreen filter comprising avobenzone and at least one additional organic sunscreen filter selected from the group consisting of octocrylene, homosalate and octisalate; and
    an alkyl benzoate comprising 25-55 mole % C12-14 alkyl benzoate and 45-75 mole % C12-C15 alkyl benzoate;
    and wherein said organic sunscreen formulation has a critical wavelength of at least 370 nm.

15. The sunscreen formulation of claim 14 comprising 5-75 wt % said organic sunscreen filter and 25-95 wt % said alkyl benzoate.

16. The sunscreen formulation of claim 15 comprising 30-60 wt % said organic sunscreen filter and 40-70 wt % said alkyl benzoate.

17. The sunscreen formulation of claim 14 comprising at least 22 mole % to no more than 67 mole % C12 alkyl benzoate.

18. The sunscreen formulation of claim 14 wherein said at least one additional organic sunscreen filter is octocrylene.

19. The sunscreen formulation of claim 14 wherein said at least one additional organic sunscreen filter is homosalate.

20. The sunscreen formulation of claim 14 wherein said at least one additional organic sunscreen filter is octisalate.

21. The sunscreen formulation of claim 14 wherein said C12-C14 alkyl benzoate comprises at least 65 to no more than 75 mole % C12 alkyl benzoate and at least 21 to no more than 28 mole % C14 alkyl benzoate and no more than 10 mole % C16 alkyl benzoate.

22. The sunscreen formulation of claim 14 wherein said C12-C15 alkyl benzoate comprises at least 15 to no more than 35 mole % C12 alkyl benzoate; at least 15 to no more than 35 mole % C13 alkyl benzoate; at least 15 to no more than 35 mole % C14 alkyl benzoate and at least 15 to no more than 35 mole % C15 alkyl benzoate.

23. The sunscreen formulation of claim 14 wherein said critical wavelength is at least 380 nm.

24. The sunscreen formulation of claim 23 wherein said critical wavelength is at least 382 nm.

* * * * *